(12) United States Patent
O'Lenick, Jr.

(10) Patent No.: US 8,268,766 B1
(45) Date of Patent: Sep. 18, 2012

(54) POLYMERIC SURFACTANTS BASED UPON ALKYL POLYGLYCOSIDES AND SORBITAN ESTERS

(75) Inventor: Anthony J. O'Lenick, Jr., Dacula, GA (US)

(73) Assignee: Surfatech Corporation, Lawrenceville, GA (US)

( * ) Notice: Subject to any disclaimer, the term of this patent is extended or adjusted under 35 U.S.C. 154(b) by 237 days.

(21) Appl. No.: 12/653,458

(22) Filed: Dec. 16, 2009

Related U.S. Application Data

(60) Provisional application No. 61/276,301, filed on Sep. 11, 2009.

(51) Int. Cl.
- *C11D 17/00* (2006.01)
- *C11D 3/37* (2006.01)
- *C11D 1/66* (2006.01)
- *A61K 8/00* (2006.01)
- *A61K 8/73* (2006.01)
- *A61K 8/02* (2006.01)
- *A61Q 1/14* (2006.01)
- *C07H 1/00* (2006.01)

(52) U.S. Cl. ........ 510/151; 510/119; 510/121; 510/475; 510/130; 510/470; 510/474; 424/401; 424/70.13; 536/124

(58) Field of Classification Search .................. None
See application file for complete search history.

(56) References Cited

U.S. PATENT DOCUMENTS

| | | | | |
|---|---|---|---|---|
| 2,285,422 A | * | 6/1942 | Epstein et al. | 516/73 |
| 4,035,513 A | * | 7/1977 | Kumano | 514/785 |
| 7,507,399 B1 | * | 3/2009 | O'Lenick, Jr. | 424/70.11 |
| 2004/0009199 A1 | * | 1/2004 | Dee et al. | 424/401 |

OTHER PUBLICATIONS

Hill, K., et al., "Alkyl Polyglycosides", 1997, VCH Verlagsgesellschaft, pp. 82-84.*
Balzer, D., et al., "Nonionic Surfactants: Alkyl Polyglucosides", 2000, surfactant science series, 91, pp. 1-2.*
"Starch Brightens detegrents Market", accessed: http://www.icis.com/Articles/1994/08/01/24606/starch-brightens-detergents-market.html, Aug. 1994, pp. 1-2.*

* cited by examiner

*Primary Examiner* — Michael G Hartley
*Assistant Examiner* — Lance Rider

(57) ABSTRACT

The present invention relates to a series of polyglycoside derivatives that are (a) polymeric (that is cross linked with hydroxypropyl linkages) and (b) contain additional functional groups including alkoxy, sulfate, sulfonate, quaternary and phosphate groups, and (c) sorbitan esters to increase oil solubility and provide outstanding emulsifiers.

19 Claims, No Drawings

POLYMERIC SURFACTANTS BASED UPON ALKYL POLYGLYCOSIDES AND SORBITAN ESTERS

RELATED APPLICATIONS

This application claims priority to and benefit of U.S. Provisional Application No. 61/276,301 filed Sep. 11, 2009, the disclosure of which is incorporated herein for all purposes.

FIELD OF THE INVENTION

The present invention relates to a series of polyglycoside derivatives that are (a) polymeric (that is cross linked with hydroxypropyl linkages) and (b) contain additional functional groups including alkoxy, sulfate, sulfonate, quaternary and phosphate groups, and (c) sorbitan esters to increase oil solubility and provide outstanding emulsifiers.

Commercial alkyl polyglycosides generally have a low degree of polymerization of polysaccharide, in the molecule. This results in a molecule that is of limited water solubility, and essentially no emulsification properties. The present invention is aimed at functionalizing the hydrophobic alkyl polyglycoside, making them even more hydrophobic and surprisingly emulsifiers. The raw materials upon which these materials are based have been called "alkyl glycosides, alkyl glycosides, alkyl polyglycosides or alkyl polyglycosides" by many different authors. All refer to the same molecules.

BACKGROUND

Alkyl polyglycosides have been known for many years, having been first synthesized in the early 1900 by Emile Fischer. Despite this, the products were of little commercial interest until much later.

U.S. Pat. No. 4,393,203 issued Jul. 12, 1983 to Mao et al, incorporated herein by reference, disclose that long chain fatty alcohols can be removed from alkyl polysaccharide products in thin film evaporators to achieve fatty alcohol levels of less than about 2% without excessive discoloration of the alkyl polysaccharide. This allowed for a more cosmetically acceptable product to be developed that is more surface active. The presence of the free fatty alcohol in the mixture, allows for a more water-soluble product, by removing the water insoluble alcohol.

One of the most significant patents is U.S. Pat. No. 5,003,057 issued Mar. 26, 1991 to McCurry et al incorporated herein by reference, provides for a process for preparing glycosides from a source of saccharide moiety and an alcohol in the presence of a hydrophobic acid catalyst is provided. An example of such a catalyst is dinonylnaphthalenemonosulfonic acid. The use of such catalysts provides a number of process advantages, which includes the reduced production of polar by-products. Preferred glycosides produced by the process are higher alkyl glycosides useful as surfactants.

U.S. Pat. No. 3,598,865 (Lew) discloses the production of higher alkyl ($C_{-8}$-$C_{25}$) glycosides from a monosaccharide or source thereof and a higher monohydric alcohol in the presence of a latent solvent (lower alcohols) and an acid catalyst selected from the group consisting of sulfuric acid, hydrochloric acid, phosphoric acid, phosphorous acid, toluenesulfonic acid, and boron trifluoride.

U.S. Pat. No. 3,219,656 (Boettner) discloses a process for producing a higher alkyl glycoside by reacting glucose with methanol in the presence of a macroreticular-structured sulfonic acid resin, anhydrous and in the acid form, to produce methyl glycoside which is reacted without isolation with butanol to form butyl glycoside and which in turn is reacted with a higher alcohol to form a surface active higher alkyl glycoside.

U.S. Pat. No. 3,839,319 (Mansfield) discloses a process for producing alkyl glycosides by direct, acid catalyzed reaction of a higher alcohol and a saccharide. The acid catalysts are mineral acids such as hydrochloric and sulfuric, and sulfonic acid exchange resins The compounds known before the current invention have been primarily used in industrial applications like detergents for dish wash. This is due in part to inherent drying that occurs when these materials are applied to the skin. Many people, one of which is Cognis, have introduced blends of alkyl polyglycosides and traditional surfactants to overcome these limitations. The blending of other alternative surfactants, while demonstrating a long felt need for improvement in the performance of the product, does not address underlying difficulties in the molecule.

U.S. Pat. No. 4,297,290 to Stockberger issued Oct. 27, 1981 teaches that sorbitan fatty acid esters can be prepared by forming anhydro sorbitol (a mixture of sorbitans, isosorbide, and unreacted sorbitol) by acid-catalyzed anhydrization, then reacting the resulting anhydro sorbitol with a fatty acid in the presence of a base at a temperature not exceeding about 215° C. Use of temperatures not over 215° C. results in products having substantially less color than those obtained at higher temperatures. It is these hydrophobic materials that are the raw material for synthesis of the emulsifiers of the present invention.

U.S. Pat. No. 7,556,653 to LaVay et al issued Jul. 7, 2009 entitled Polymeric silicone alkoxyglyceryl softeners teaches a class of polyesters that are lightly crosslinked polyesters made by reacting alkoxy glyceryl units (linked by the reaction of their hydroxyl groups) to the carboxyl group of dimer acid. As will become clear, lightly crosslinked as used herein relates to reactions in which there is an excess of hydroxyl groups on a molar basis to carboxylic groups on the dimer acid. The polymers and a contribute softness, lubricity and antistatic properties when applied to hair, skin, textile fiber and paper. This patent teaches that dimer acid can be used to crosslink polysorbates to make conditioners. This patent provides conditioners not emulsifiers, and lacks the critical element of alkyl polyglycoside and crosslinker.

U.S. Pat. No. 7,507,399 issued Mar. 24, 2009 to O'Lenick entitled Functionalized polymeric surfactants based upon alkyl polyglycosides teaches a series of multifunctional polyglycosides derivatives that are made by the polymerized by the reaction of 1,3 dichloro isopropanl and polyglycosides, together with a functionalizing agent that contains a sulfate, sulfonate, quaternary nitrogen, or a phosphate group. This patent lacks the critical element of the sorbitan ester to make an emulsifier.

All patents referenced above are incorporated herein by reference. None of the patents referenced above either alone or combination teach or suggest the making of the compounds of the present invention, namely combining the sorbitan ester with the alkylpolyglycoside and the crosslinker.

THE INVENTION

The present invention relates to the finding that the reaction of alkyl polyglycosides, sorbitan esters and the proper additional reagent results in molecules that is an excellent emulsifier. It is most interesting that the maximum amount of glycoside units per alkyl group that can be added using known technology is 1.5. This means that the product is a mixture of mono and di functional product. This product has the remaining fatty alcohol stripped off in an evaporative process. The resulting product is about 70% by weight of a product of a d.p. of 1, about 21% by weight of a product of a d.p. of 2, about 7% by weight of a product having a d.p. of 3, and about 2% by weight of a product that has a d.p. of 4.

We have surprisingly learned that taking the alkyl polyglycosides produced in the commercial process, with its inherent properties to make them emulsifiers even when cross linked polymers, and include functional groups, including alkoxy, sulfate, sulfonate, quaternary and phosphate groups results in a series of products that are much more usable in many applications.

SUMMARY OF THE INVENTION

Alkyl polyglycosides are complex products made by the reaction of glucose and fatty alcohol. In dealing with the chemistry one talks about degree of polymerization (the so called "d.p."). In the case of traditional alkyl polyglycosides the d.p. is around 1.4. This means that on average there is 1.4 units of glucose for each alkyl group. The fact of the matter is that the resulting material is a mixture having an average of 1.4.

The specific structure of the product is hard to ascertain completely since many positional isomers are possible, but two examples of structures are as follows;

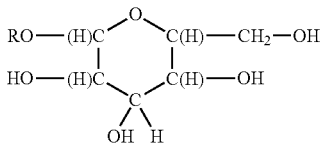

Alkyl polyglycosides (d.p. 1)

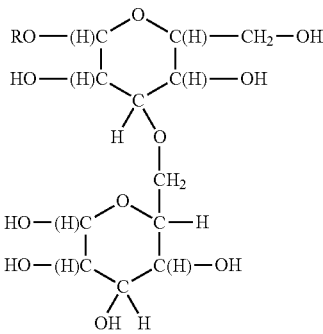

Alkyl polyglycosides (d.p. 2)

It should be clear that if there is a 50/50 mixture of the d.p. 1 and d.p. 2 product, the resulting analytical data will show that on average there is a d.p. of 1.5. Saying that a molecule has a d.p. of 1.5 does not mean that each molecule has 1.5 glucose units on it.

One key aspects of the present invention relates to the heretofore unappreciated fact that by polymerizing the alkyl polyglycosides together with specific hydrophobic sorbitan esters using the process specified in U.S. Pat. No. 7,507,399 issued Mar. 24, 2009 to O'Lenick entitled Functionalized polymeric surfactants based upon alkyl polyglycosides provides a route to outstanding emulsifiers free of ethylene and propylene oxide.

Another key unappreciated fact in making the compounds of the present invention is the selection of the proper reagents to make the desired product. Specifically, the reaction of the alkyl polyglycoside together with the sorbitan ester with a certain family of epoxy compounds and related materials occurs under mild aqueous conditions and results in an outstanding emulsifier derived from natural ingredients.

DETAILED DESCRIPTION OF THE INVENTION

The compositions of the present invention are prepared by reacting the mixtures conform to the following structures:

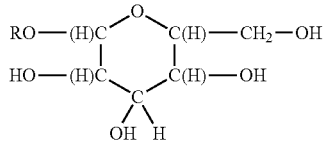

(a)

wherein;
R is alkyl having 8 to 22 carbon atoms;
and

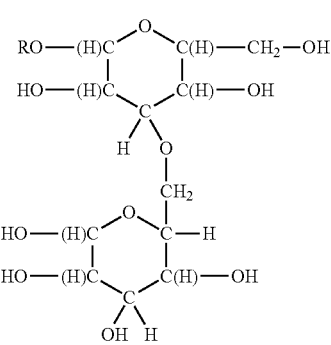

(b)

wherein;
R is alkyl having 8 to 22 carbon atoms;
(c) a sorbitan ester conforming to the following structure:

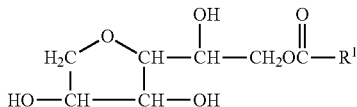

$R^1$ is alkyl having from 7 to 21 carbon atoms;
with a polymerizing agent conforming to the following structure
$Cl—CH_2CH(OH)CH_2Cl$
and
optionally a functionalizing agent selected from the group consisting of

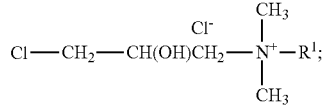

$Cl—CH_2—CH(OH)—SO_3M$;
$Cl—CH_2—CH(OH)CH_2—SO_4M$;
$Cl—CH_2—CH(OH)—CH_2—OP(O)—(OM)_2$;
and mixtures thereof;
wherein:
$R^1$ is $CH_3—(CH_2)$
n is an integer ranging from 6 to 36;
M is needed for charge balance and is selected from the group consisting of
H, Na, K, or $NH_4$.

It will become clear that the compositions of the present invention need to be claimed as product by process, since they are the reaction product of two multi-hydroxyl product (alkyl polyglycosides and sorbitan esters) and a di-chloro intermediate. Since there is not a great deal of group specificity in the reaction of the various hydroxyl groups, cross linked polymers result. The degree of cross linking depends upon the ratio of 1,3 dichloro isopropanol to hydroxyl groups chosen. The functionalizing agent likewise reacts with hydroxyl groups, providing a multifunctional polymer.

By considering the reaction in steps, it will make the reaction pathway clearer.

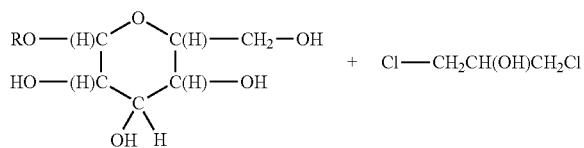

The 1,3 dichloro-isopropanol reacts with the first hydroxyl group giving an intermediate:

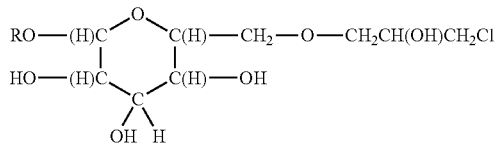

The above reaction shows only one of the possible reacted hydroxyl groups on one hydroxyl rich compound, the alkyl polyglycoside. There is an equal potential for reaction of the other hydroxyl groups on the alkyl polyglycoside and the sorbitan ester as well, and in fact there if formed a random polymer of sorbitan ester units and alkyl poylglycoside units having a hydroxy propyl linkage. Subsequently, another hydroxyl group reacts to give:

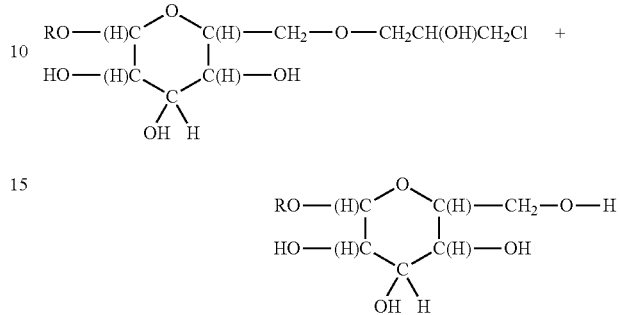

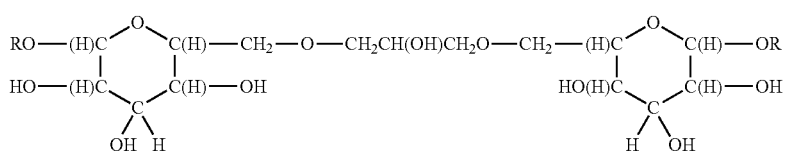

Functionalization

The optional functionalization group is added to one of the additional hydroxyl groups for example:

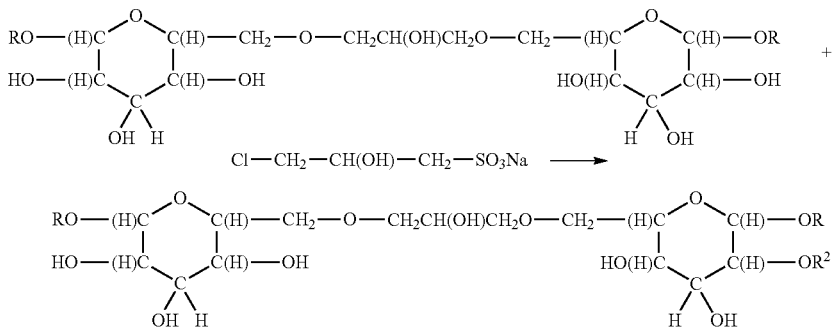

wherein
$R^2$ is —$CH_2$—$CH(OH)$—$CH_2$—$SO_3Na$.

As the reaction continues more and more hydroxyl groups react, coming from the alkyl poylglycoside and the sorbitan ester with either the polymerizing agent or the functionalizing agent. The structure is complicated not only by the fact that many hydroxyl groups, on APG (alkyl polyglycoside) or on sorbitan ester can react with the different types of agent, but also by the fact that commercial polyglycosides are mixtures having an average dp of 1.5. The resulting products are hydroxypropyl cross linked polymers having branching present. This is the reason for claiming the products in a product by process format.

Another aspect of the present invention is a process for conditioning hair and skin which comprises contacting the hair and skin with an effective conditioning concentration of a composition prepared by reacting a composition conforming to the following:

(a)
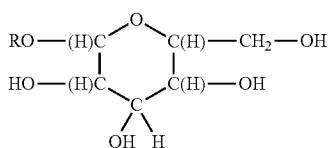

wherein;
R is alkyl having 8 to 22 carbon atoms;
and (b)
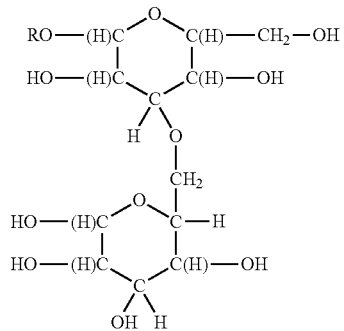

wherein;
R is alkyl having 8 to 22 carbon atoms;
and
(c) a sorbitan ester conforming to the following structure:

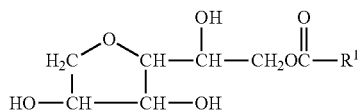

$R^1$ is alkyl having from 7 to 21 carbon atoms;
with a polymerizing agent conforming to the following structure
Cl—CH$_2$CH(OH)CH$_2$Cl
and
optionally a functionalizing agent selected from the group consisting of:

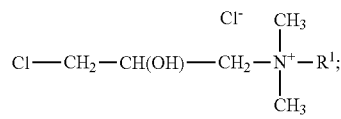

Cl—CH$_2$—CH(OH)—SO$_3$M;
Cl—CH$_2$—CH(OH)CH$_2$—SO$_4$M;
Cl—CH$_2$—CH(OH)—CH$_2$—OP(O)—(OM)$_2$;
and mixtures thereof;
wherein:
$R^1$ is CH$_3$—(CH$_2$)$_n$—
n is an integer ranging from 6 to 36;
M is needed for charge balance and is selected from the group consisting of
H, Na, K, or NH$_4$.

Preferred Embodiment

In a preferred embodiment the functionalizing agent is:

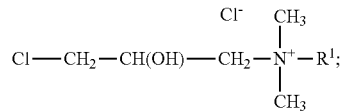

$R^1$ is CH$_3$—(CH$_2$)$_n$—
n is an integer ranging from 6 to 36.
In a preferred embodiment n is 11.
In a preferred embodiment n is 13.
In a preferred embodiment n is 15.
In a preferred embodiment n is 17.
In a preferred embodiment n is 19.
In a preferred embodiment n is 35.
In another preferred embodiment the functionalizing agent is
Cl—CH$_2$—CH(OH)—SO$_3$M
M is needed for charge balance and is selected from the group consisting of
H, Na, K, or NH$_4$.
In another preferred embodiment the functionalizing agent is
Cl—CH$_2$—CH(OH)CH$_2$—SO$_4$M
M is needed for charge balance and is selected from the group consisting of
H, Na, K, or NH$_4$.
In another preferred embodiment the functionalizing agent is
Cl—CH$_2$—CH(OH)—CH$_2$—OP(O)—(OM)$_2$
M is needed for charge balance and is selected from the group consisting of
H, Na, K, or NH$_4$.
In a preferred embodiment the functionalizing agent is a mixture of;

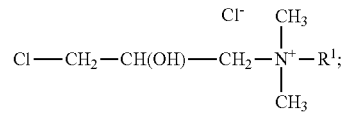

Cl—CH$_2$—CH(OH)—SO$_3$M;
Cl—CH$_2$—CH(OH)CH$_2$—SO$_4$M;
and
Cl—CH$_2$—CH(OH)—CH$_2$—OP(O)—(OM)$_2$;
wherein:
$R^1$ is CH$_3$—(CH$_2$)$_n$—
n is an integer ranging from 5 to 35;
M is needed for charge balance and is selected from the group consisting of
H, Na, K, or NH$_4$.
In a preferred embodiment the effective conditioning concentration ranges from 0.1 to 25% by weight.
In a preferred embodiment the effective conditioning concentration ranges from 1% to 15% by weight.

EXAMPLES

Preparation of Alkyl Glycosides

Alkyl Glycosides are raw materials used to make the surface-active polyglycoside derivatives of the present invention.
Saccharides useful in the process of making alkyl glycosides are saccharides that can be alkylated in the "1" position, commonly referred to as "reducing saccharides", or higher saccharides that can be hydrolyzed to provide such a saccharide. These saccharides are typically comprised of aldo- or keto-hexoses or pentoses.
Examples of saccharides include glucose (dextrose), fructose, mannose, galactose, talose, allose, altrose, idose, arabinose, xylose, lyxose, and ribose. Examples of hydrolyzable saccharides that are a source of reducing saccharides include starch, maltose, sucrose, lactose, maltotriose, xylobiose, mellibiose, cellobiose, raffinose, stachiose, methyl glycosides, butyl glycosides, levoglucosan, and 1,6-anhydroglucofuranose.

The physical form of the saccharide may vary. The saccharide will typically be in a fluid (as opposed to a solid) state, e.g. as a melt or an aqueous syrup, during at least a portion of the period of reaction, if not for a predominant portion of the period of the reaction. Crystalline (e.g. anhydrous or hydrates) or amorphous saccharide solids in various particle sizes, e.g. granules, powders, etc., can be used, but the heating of the reaction medium may well fluidize at least a portion of a solid reactant, if not a predominant portion of the saccharide reactant. Aqueous syrups of saccharides, typically at saccharide solids of between about 10% and 90% dry solids by weight can also be used. Indeed, the use of the hydrophobic catalysts of this invention should show the most improved results over conventional catalysts in the context of the use of aqueous syrup reactants as compared with processes which employ solid saccharide reactants, particularly with respect to avoiding the formation of deleterious amounts of polysaccharides and very high DP alkyl glycosides during the glycoside formation reaction.

The preferred saccharides are glucose, galactose, xylose and arabinose, or mixtures thereof, for reasons of availability, low cost, and convenience. Glucose in the anhydrous crystalline form is preferred, although dextrose monohydrate, corn syrups of high dry solids (typically 50% to 80% dry solids) and a high dextrose equivalence (D.E.) (typically greater than 90 D.E and most commonly 95 D.E.) can be commonly employed. Indeed, while the higher the purity of the dextrose source, the better the quality of the product (other things being equal), the catalysts of this invention allow the use of a lower purity dextrose source and yet yield a product of substantially equivalent quality as compared with prior catalysts. Because of the ready availability of glucose and its oligomers, much of the remaining description is particularly suited to the use of glucose in its various forms.

Alcohols useful in the process of this invention are hydroxyl-functional organic compounds capable of alkylating a saccharide in the "1" position. The alcohol can be naturally occurring, synthetic, or derived from natural sources and/or derivatized. Examples include monohydric alcohols (more fully discussed below) and polyhydric alcohols (e.g. ethylene glycol, propylene glycol, polyethylene glycols, polypropylene glycols, butylene glycol, glycerol, trimethylolpropane, pentaerythritol, polyester polyols, polyisocyanate polyols, and so on). Other examples include aromatic alcohols such as benzyl alcohol, phenol, substituted phenols (e.g. alkylphenols) and alkoxylates of each.

Preferred alcohols are monohydric alcohols containing from about 1 to about 30 carbon atoms. They may be primary or secondary alcohols, straight or branched chain, saturated or unsaturated (e.g. allyl alcohol, 2-ethylhexenyl alcohol and oleyl alcohol) alkyl or aralkyl alcohols, ether alcohols, cyclic alcohols, or heterocyclic alcohols. In general, these alcohols have minimal solvent power for the saccharide molecule. Examples of the monohydric alcohols which may be employed in the present invention include methyl alcohol, isopropyl alcohol, butyl alcohol, octyl alcohol, nonyl alcohol, decyl alcohol, dodecyl alcohol, tridecyl alcohol, tetradecyl alcohol, pentadecyl alcohol, hexadecyl alcohol, pentacosyl alcohol, oleyl alcohol, linoleyl alcohol, isoborneol alcohol, hydroabietyl alcohol, phenoxyethanol, phenoxypolyethoxyethanol containing five ethoxy groups, 2-methyl-7-ethyl-4-undecanol, and mixtures of one or more of the above.

A preferred group of alcohols are alkanols having the formula ROH wherein R represents an alkyl group having from 8 to 30 carbon atoms. A particularly preferred group of alcohols are those wherein R represents an alkyl radical having from 8 to 20, preferably 11 to 18, carbon atoms. The alkyls can be straight or branched chain.

Alkyl Glycoside Examples

Example 1

A one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 602.4 g (3.105 moles) of a commercial mixture of $C_{11}$ to $C_{15}$ (98% $C_{12}$ and $C_{13}$) straight and branched alkanols (Neodol 23 available form Shell Chemical Co.) and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57.degree. C. and heating was continued until the slurry had reached 110.degree. C. At this time 3.2 g (0.00345 mole of a commercially available mixture of 50% dinonylnaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in $H_2O$) was added. An aliquot of the neutralized reaction mixture (3.39 g, 1 g dissolved substance) was dissolved in a total volume of 10 ml with 1:1 isopropanol:water. The pH of this solution was 7.8.

The remainder of the reaction mixture was evaporated to a clear melt at 200.degree. C. and 1 mm pressure using a Leybold-Heraeus Distact™ wiped film evaporator operating at a feed rate of 700 ml/hr.

The residue was analyzed using a combination of gas and liquid chromatographic techniques as well as NMR spectroscopy and was shown to contain less than 0.2% free alcohol and less than 2% polar species (HPLC) and an NMR mole ratio of glucose rings to fatty chains of about 1.4.

Example 2-9

The same one-liter, four-necked, round-bottomed flask was equipped through its center neck with an overhead mechanical stirrer, through a second neck with a distillation head fitted with an addition funnel and a condenser/receiver/vacuum take-off assembly, through a third neck fitted with a three hole rubber stopper with a capillary nitrogen bleed, a calibrated mercury thermometer and a vacuum tight temperature controller probe, and on the fourth neck with a septum for sampling.

The flask was charged with 3.105 moles of the specified alcohol and 136.6 g (0.69 moles) of a commercially available dextrose monohydrate (Staleydex 333, available from A. E. Staley Mfg. Co. at 9.0% moisture). The slurry was heated at a vacuum of 30 mm Hg (absolute). Water was released starting at about 57.degree. C. and heating was continued until the slurry had reached 110.degree. C. At this time 3.2 g (0.00345 mole of a commercially available mixture of 50% dinonylnaphthalenesulfonic acid in heptane (available from King Industries) was added as a catalyst and the theoretical volume of water distilled at about a linear rate over 8 hours. After stirring an additional hour, a stoichiometric amount of aqueous NaOH (33% in H$_2$O) was added. An aliquot of the neutralized reaction mixture (3.39 g, 1 g dissolved substance) was dissolved in a total volume of 10 ml with 1:1 isopropanol:water. The pH of this solution was 7.8.

The remainder of the reaction mixture was evaporated to a clear melt at 200.degree. C. and 1 mm pressure using a Leybold-Heraeus Distact™ wiped film evaporator operating at a feed rate of 700 ml/hr.

The residue was analyzed using a combination of gas and liquid chromatographic techniques as well as NMR spectroscopy and was shown to contain less than 0.2% free alcohol and less than 2% polar species (HPLC) and an NMR mole ratio of glucose rings to fatty chains of about 1.4. The hydroxyl value was run on the resultant product and is indicated below.

| Example | Alkyl | OH Value |
|---|---|---|
| 2 | C$_{12}$H$_{25}$ | 691.9 |
| 3 | C$_{10}$H$_{21}$ | 741.8 |
| 4 | C$_8$H$_{17}$ | 795.4 |
| 5 | C$_{14}$H$_{27}$ | 653.8 |
| 6 | C$_{18}$H$_{37}$ | 584.4 |
| 7 | C$_{18}$H$_{35}$ | 586.7 |
| 8 | C$_{20}$H$_{42}$ | 555.1 |
| 9 | C$_{22}$H$_{42}$ | 531.2 |

Sorbitan Esters of Fatty Acids (Sorbitan Ester)

Sorbitan esters of fatty acid is called sorbitan ester, which is produced by esterification of sorbitol and fatty acid. It is a mixture of sorbitol ester and sorbide ester, which are simultaneously produced as well as sorbitan ester. There are many types of sorbitan esters with different kinds of fatty acids and various degrees of esterification.

Commercially available materials come from a variety of suppliers including Croda. The following is taken from their catalogue:

| Product | Chemical composition | HLB | Color and form at 25° C.[1] | Viscosity at 25° C. or pour point[2] |
|---|---|---|---|---|
| Span 20 | Sorbitan monolaurate | 8.6 | Amber liquid | 4250 cs |
| Span 40 | Sorbitan monopalmitate | 6.7 | Tan solid | 48° C. |
| Span 60[3] | Sorbitan monostearate | 4.7 | Tan solid | 53° C. |
| Span 60K (Kosher grade) | Sorbitan monostearate | 4.7 | Tan sold | 53° C. |
| Span 65 | Sorbitan tristearate | 2.1 | Cream solid | 53° C. |
| Span 80 | Sorbitan monooleate | 4.3 | Amber liquid | 1000 cs |
| Span 85 | Sorbitan trioleate | 1.8 | Amber liquid | 210 cs |

The above products are listed as examples of products but the products used in the preparation of the compounds of the present invention were verified by wet analysis and proton and C13 nm r so they are independent of trade names.

Sorbitan ester useful as raw materials for the preparation of the compounds of the present invention conform to the following structure:

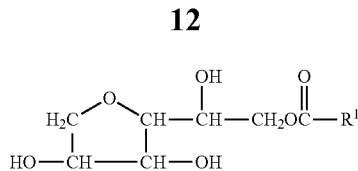

R$^1$ is alkyl having from 7 to 21 carbon atoms;

Examples 10-16

| Example | R$^1$ |
|---|---|
| 10 | 7 |
| 11 | 9 |
| 12 | 11 |
| 13 | 13 |
| 14 | 15 |
| 15 | 17 |
| 16 | 21 |

Alkyl Polyglycosides Functionaized Products

There are a number of groups that can be introduced into the finished alkyl polyglycoside/sorbitol ester copolymer. These include phosphates; sulfates, alkoxylate and quaternary groups.

It will be clearly understood that the alkyl polyglycoside/sorbitan ester copolymer of the present invention have a number of hydroxyl groups present in the molecule. The number of hydroxyl groups functionalized will have a profound effect upon the degree of increased water solubility of the molecule.

The present invention includes a functionalization of a low number of hydroxyl groups (one per molecule) to a high number (all groups on the molecule). The preferred number to functionalize is an intermediate number of groups (approximately half of the number present).

Example 17

1,3 Dichloro Isopropanol

The polymerizing agent of the present invention is;
Cl—CH$_2$CH(OH)CH$_2$Cl (1,3 dichloro isopropanol)
1,3 dichloro isopropanol is an item of commerce commercially available from Dixie Chemical.

Example 18

Chloro Hydroxypropyl Sulfonate

The product conforms to the following structure:
Cl—CH$_2$—CH(OH)CH$_2$—SO$_3$Na.
It is an item of commerce available from Siltech Corporation in Toronto Canada.

Example 19

Chloro Hydroxypropyl Sulfate

The product conforms to the following structure:
Cl—CH$_2$—CH(OH)CH$_2$—SO$_4$K.
It is an item of commerce available from Siltech Corporation in Toronto Canada.

Example 20

Chloro Hydroxypropyl Phosphate

The product conforms to the following structure:
Cl—CH$_2$—CH(OH)CH$_2$—O—P(O)O Na.
It is an item of commerce available from Siltech Corporation in Toronto Canada.
Chloro Hydroxypropyl Quat
The product conforms to the following structure:

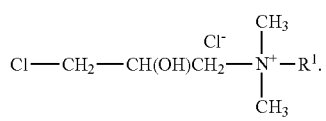

It is an item of commerce available from Siltech Corporation in Toronto Canada.

| Example | n Value |
|---------|---------|
| 21 | 5 |
| 22 | 11 |
| 23 | 15 |
| 24 | 17 |
| 25 | 21 |
| 26 | 35 |

General Procedure—To a flask equipped with agitation, heat, thermometer and nitrogen sparge is added the specified amount of the specified alkyl polyglycoside (example 1-9), the specified amount of the specified sorbitan ester (example 10-16) and enough water to make the final product have a solids of 35% by weight. Next, the specified amount of 1,3 dichloro isopropanol is (Example 17) added under good agitation and nitrogen sparge. Next is added 0.5% sodium methylate. Next add the specified number of grams of the specified functionalizing agent (Examples 18-26). The % is by weight and is based upon the total amount of all materials reacted. Nitrogen sparge is simply nitrogen bubbled through the liquid contents of the flask. This keeps the color light, minimizing oxidation and color formation. The reaction mass is heated to 90-100° C., and is held for 5-8 hours. The reaction progress is monitored by formation of chloride ion. Once the theoretical value is reached, the reaction is terminated and the product is used without additional purification.

Example 27-37

| | APG | | Sorb Ester | | Ex 17 | Functionalizing Agent | |
|---------|----|-------|----|-------|-------|---------|-------|
| Example | Ex | Grams | Ex | Grams | Grams | Example | Grams |
| 27 | 1 | 246.0 | 10 | 200.0 | 65.0 | 18 | 130.0 |
| 28 | 2 | 116.0 | 11 | 300.0 | 65.0 | 19 | 150.0 |
| 29 | 3 | 288.0 | 12 | 100.0 | 65.0 | 20 | 150.0 |
| 30 | 4 | 322.0 | 13 | 150.0 | 65.0 | 21 | 130.0 |
| 31 | 5 | 328.0 | 14 | 200.0 | 65.0 | 22 | 130.0 |
| 32 | 6 | 400.0 | 15 | 126.0 | 65.0 | 23 | 65.0 |
| 33 | 1 | 300.0 | 16 | 146.0 | 198.0 | 24 | 130.0 |
| 34 | 2 | 216.0 | 15 | 200.0 | 198.0 | 25 | 150.0 |
| 35 | 3 | 288.0 | 14 | 100.0 | 198.0 | 26 | 200.0 |
| 36 | 4 | 300.0 | 13 | 175.0 | 132.0 | 18 | 180.0 |
| 37 | 5 | 328.0 | 12 | 200.0 | 330.0 | 19 | 160.0 |

The compounds of the invention range from clear yellow liquids to pastes. They are outstanding emulsifiers for making water in oil and oil in water emulsions.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:
1. A composition prepared by reacting:

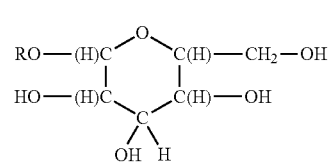

wherein;
R is alkyl having 8 to 22 carbon atoms;
and

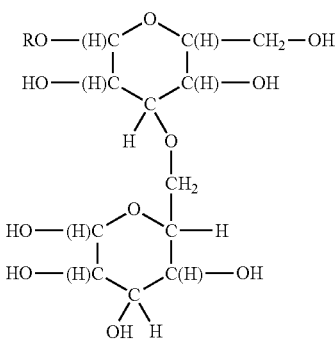

wherein;
R is alkyl having 8 to 22 carbon atoms;
(c) a sorbitan ester conforming to the following structure:

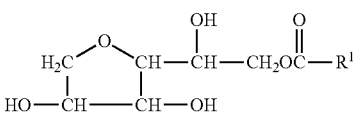

R$^1$ is alkyl having from 7 to 21 carbon atoms;
with a polymerizing agent conforming to the following structure
Cl—CH$_2$CH(OH)CH$_2$Cl
in water:
and
optionally a functionalizing agent selected from the group consisting of:

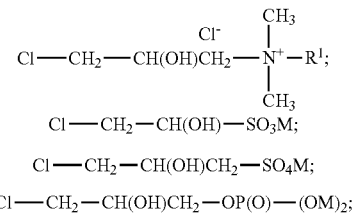

and mixtures thereof;
wherein:
$R^1$ is $CH_3$—$(CH_2)_n$—
n is an integer ranging from 6 to 36;
M is needed for charge balance and is selected from the group consisting of
H, Na, K, or $NH_4$.

2. A composition of claim 1 wherein n is 13.
3. A composition of claim 1 wherein n is 15.
4. A composition of claim 1 wherein n is 17.
5. A composition of claim 1 wherein n is 19.
6. A composition of claim 1 wherein n is 35.
7. A composition of claim 1 wherein the functionalizing agent is
Cl—$CH_2$—CH(OH)—$SO_3M$
M is needed for charge balance and is selected from the group consisting of
H, Na, K, or $NH_4$.
8. A composition of claim 1 wherein the functionalizing agent is
Cl—$CH_2$—CH(OH)$CH_2$—$SO_4M$
M is needed for charge balance and is selected from the group consisting of
H, Na, K, or $NH_4$.
9. A composition of claim 1 wherein the functionalizing agent is
Cl—$CH_2$—CH(OH)—$CH_2$—OP(O)—$(OM)_2$
M is needed for charge balance and is selected from the group consisting of
H, Na, K, or $NH_4$.
10. A composition of claim 1 wherein the functionalizing agent is a mixture of;

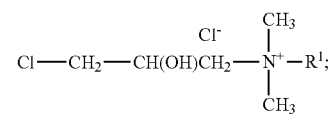

Cl—$CH_2$—CH(OH)—$SO_3M$;
Cl—$CH_2$—CH(OH)$CH_2$—$SO_4M$;
and
Cl—$CH_2$—CH(OH)—$CH_2$—OP(O)—$(OM)_2$;
wherein:
$R^1$ is $CH_3$—$(CH_2)_n$—
n is an integer ranging from 5 to 35;
M is needed for charge balance and is selected from the group consisting of
H, Na, K, or $NH_4$.

11. A process for conditioning hair or skin which comprises contacting the hair or skin with an effective conditioning concentration of a composition prepared by reacting:

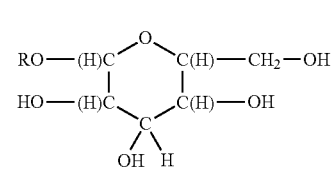

wherein;
R is alkyl having 8 to 22 carbon atoms;
and

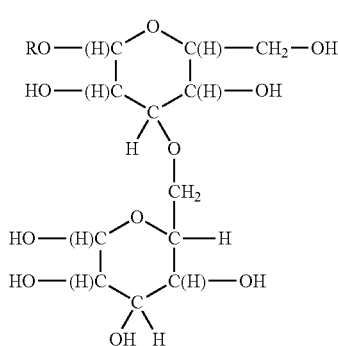

wherein;
R is alkyl having 8 to 22 carbon atoms;
(c) a sorbitan ester conforming to the following structure:

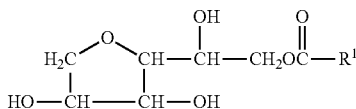

$R^1$ is alkyl having from 7 to 21 carbon atoms;
with a polymerizing agent conforming to the following structure
Cl—$CH_2CH(OH)CH_2Cl$
in water:
and
optionally a functionalizing agent selected from the group consisting of:

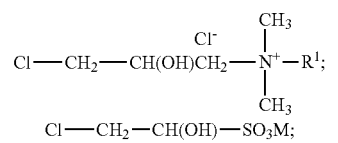

and mixtures thereof;
wherein:
$R^1$ is $CH_3$—$(CH_2)_n$—
n is an integer ranging from 6 to 36;
M is needed for charge balance and is selected from the group consisting of
H, Na, K, or $NH_4$.

12. A process of claim 11 wherein the effective conditioning concentration ranges from 0.1 to 25% by weight.

13. A process of claim 11 wherein the effective conditioning concentration ranges from 1% to 15% by weight.

14. A process of claim 12 wherein the functionalizing agent is:

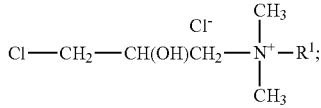

$R^1$ is $CH_3$—$(CH_2)_n$— n is an integer ranging from 6 to 36.

15. A process of claim 12 wherein the functionalizing agent is

Cl—$CH_2$—CH(OH)—$SO_3$M

M is needed for charge balance and is selected from the group consisting of

H, Na, K, or $NH_4$.

16. A process of claim 12 wherein the functionalizing agent is

Cl—$CH_2$—CH(OH)$CH_2$—$SO_4$M

M is needed for charge balance and is selected from the group consisting of

H, Na, K, or $NH_4$.

17. A process of claim 12 wherein the functionalizing agent is

Cl—$CH_2$—CH(OH)—$CH_2$—OP(O)—$(OM)_2$

M is needed for charge balance and is selected from the group consisting of

H, Na, K, or $NH_4$.

18. A process of claim 12 wherein the functionalizing agent is a mixture of;

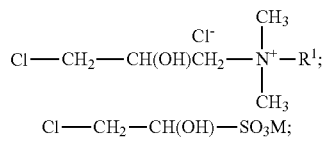

Cl—$CH_2$—CH(OH)—$SO_3$M;

Cl—$CH_2$—CH(OH)$CH_2$—$SO_4$M;

and

Cl—$CH_2$—CH(OH)—$CH_2$—OP(O)—$(OM)_2$;

wherein:

$R^1$ is $CH_3$—$(CH_2)_n$— n is an integer ranging from 5 to 35;

M is needed for charge balance and is selected from the group consisting of

H, Na, K, or $NH_4$.

19. A process of claim 13 wherein the functionalizing agent is a mixture of;

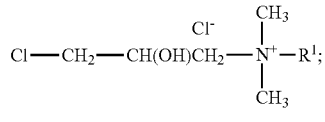

Cl—$CH_2$—CH(OH)—$SO_3$M;
Cl—$CH_2$—CH(OH)$CH_2$—$SO_4$M;
and
Cl—$CH_2$—CH(OH)—$CH_2$—OP(O)—$(OM)_2$;

wherein:

$R^1$ is $CH_3$—$(CH_2)_n$— n is an integer ranging from 5 to 35;

M is needed for charge balance and is selected from the group consisting of

H, Na, K, or $NH_4$.

* * * * *